US011000046B2

(12) United States Patent
Epiphani

(10) Patent No.: US 11,000,046 B2
(45) Date of Patent: May 11, 2021

(54) METHOD FOR MANUFACTURING AN OIL-IN-WATER EMULSION FROM AN OILY ACTIVE SUBSTANCE, FOR COSMETIC, FOOD, OR PHARMACEUTICAL USE

(71) Applicants: AR2I, Le Plessis-Robinson (FR); Jean-Claude Epiphani, Porticcio (FR)

(72) Inventor: Jean-Claude Epiphani, Porticcio (FR)

(73) Assignees: Jean-Claude, Porticcio (FR); AR2i, Le Plessis-Robinson (FR)

( * ) Notice: Subject to any disclaimer, the term of this patent is extended or adjusted under 35 U.S.C. 154(b) by 312 days.

(21) Appl. No.: 14/653,834

(22) PCT Filed: Dec. 27, 2012

(86) PCT No.: PCT/EP2012/076948
§ 371 (c)(1),
(2) Date: Jun. 18, 2015

(87) PCT Pub. No.: WO2014/101941
PCT Pub. Date: Jul. 3, 2014

(65) Prior Publication Data
US 2015/0327566 A1 Nov. 19, 2015

(51) Int. Cl.
| | |
|---|---|
| A23D 7/04 | (2006.01) |
| A61K 9/107 | (2006.01) |
| A61K 8/36 | (2006.01) |
| A61K 47/26 | (2006.01) |
| A61K 31/20 | (2006.01) |
| A61K 8/06 | (2006.01) |
| A61K 8/60 | (2006.01) |
| A61Q 19/00 | (2006.01) |
| A61K 8/92 | (2006.01) |
| A23L 29/20 | (2016.01) |

(52) U.S. Cl.
CPC ........... *A23D 7/04* (2013.01); *A23L 29/20* (2016.08); *A61K 8/062* (2013.01); *A61K 8/361* (2013.01); *A61K 8/602* (2013.01); *A61K 8/922* (2013.01); *A61K 9/107* (2013.01); *A61K 31/20* (2013.01); *A61K 47/26* (2013.01); *A61Q 19/00* (2013.01); *A23V 2002/00* (2013.01); *A61K 2800/10* (2013.01); *A61K 2800/21* (2013.01); *A61K 2800/81* (2013.01)

(58) Field of Classification Search
None
See application file for complete search history.

(56) References Cited

U.S. PATENT DOCUMENTS

| | | | | |
|---|---|---|---|---|
| 5,900,257 A | * | 5/1999 | Breton | A61P 13/00 424/639 |
| 2008/0107777 A1 | * | 5/2008 | Butler | A23L 7/198 426/71 |
| 2010/0173854 A1 | * | 7/2010 | Dominowski | A61K 9/1075 514/23 |
| 2010/0267842 A1 | | 10/2010 | Kiral et al. | |
| 2014/0057991 A1 | * | 2/2014 | Chevalier | A61K 8/37 514/678 |

FOREIGN PATENT DOCUMENTS

| | | |
|---|---|---|
| EP | 1327434 | 7/2003 |
| EP | 2359698 | 8/2011 |
| FR | 2847163 | 5/2004 |
| FR | 2945936 | 12/2010 |
| WO | WO 2004/047787 A2 | 6/2004 |
| WO | WO2004/087204 | 10/2004 |
| WO | WO2011/067672 | 6/2011 |
| WO | WO2011/154407 | 12/2011 |
| WO | WO2013/135759 | 9/2013 |

OTHER PUBLICATIONS

Machine Translation of FR2945936, 2010.*
International Search Report dated Dec. 4, 2013 from corresponding PCT Application No. PCT/EP2012/076948 from International Searching Authority (EPO) (4 pages).

* cited by examiner

*Primary Examiner* — Jianfeng Song
(74) *Attorney, Agent, or Firm* — Christensen O'Connor Johnson Kindness PLLC

(57) ABSTRACT

The invention relates to a method which includes the following steps: mixing hydrophilic components, including water and an emulsifying saponin which is less than 1% of the emulsion regardless of the proportion of the oily phase; mixing lipophilic components, including the oily active substance, which can reach 40% of the emulsion; a first homogenization of the two preceding phases using a rotor/stator or ultrasonic mixer until a mean diameter of less than 6 μm of the oily droplets is obtained; and a second homogenization of the preceding mixture using a high-pressure homogenizer until a mean diameter of less than 0.4 μm of the oily droplets is obtained.

10 Claims, No Drawings

METHOD FOR MANUFACTURING AN OIL-IN-WATER EMULSION FROM AN OILY ACTIVE SUBSTANCE, FOR COSMETIC, FOOD, OR PHARMACEUTICAL USE

SCOPE OF THE INVENTION

The present invention relates to aqueous emulsions from oily active substances for use in the cosmetic, food and pharmaceutical industries.

STATE OF THE ART TECHNOLOGY

The domains of cosmetic, food and pharmaceutical industries have a great variety of oily active substances, i.e. lipophilic or hydrophobic: vegetal oils, essential oils, fragrance concentrates, oily active substances for cosmetic, food or pharmaceutical products. It is very interesting to produce aqueous emulsions from these: oily active substances, and for one important reason: water is the most appropriate vehicle for the human body, whether externally (fragrances and cosmetic applications) or internally (food or pharmaceutical applications). Oil in water emulsions have long been produced with the aid of various chemical emulsifiers, but these emulsifiers have notorious drawbacks:—there are generally badly tolerated by the human body, —they should be used in a significant concentration with regards to the active substances. While the cyclodextrins technology is an alternative, it also imposes several constraints which greatly reduce its use. On the other hand, the use of saponins has been considered, which are vegetal emulsifiers which belong to the class of carbohydrates (heterosides). A first application category uses significant amounts of auxiliary substances (carbohydrates, ethanol, . . . . )which distort the final emulsion. A second application mode does not make use of auxiliary substances, as is provided by the patent FR 02 14436, but in practice, with a satisfactory fluidity and stability it does not allow to rise significantly beyond a concentration of 30% of the emulsion in oily phase, which is an uncomfortable limitation, specifically for certain cosmetic applications.

To date, none of the known processes have allowed the production of fluid and stable aqueous emulsions containing more than 40% of the oil phase with less than 1% of vegetable emulsifier.

DESCRIPTION OF THE INVENTION

To address the above-mentioned concerns, starting from the process described in the patent FR0214436, the applicant has explored several paths, in particular:
the use of additives (co-emulsifiers)
the implementation of all known mechanical mixing technologies
the application of various operation modes.

None of the used paths alone has achieved the intended purpose.

After several years of research and trials, the applicant has developed a process allowing for the production of aqueous emulsions from oily aqueous substances in the cosmetic, food and pharmaceutical industries, whereby such process eliminates the drawbacks of the currently applicable technologies, allowing the production of fluid and stable aqueous emulsions containing more than 40% of the oily phase with less than 1% of vegetal emulsifier. In this manner, the invention relates to the process of manufacturing an aqueous emulsion from an oily active substance for cosmetic, food or pharmaceutical use, including the following steps:
mix of hydrophilic components, including water, an emulsifying saponin, which represents less than 1% of the emulsion of whatever oily phase proportion
mix of lipophilic components, including the oily active substance, which can achieve 40% of the emulsion
homogenization n°1 of the two preceding phases with the aid of a rotor stator mixer or an ultrasonic mixer, until an average diameter of oily droplets below 6 µm is obtained
homogenization n°2 of the preceding mix with the aid of a high pressure homogenizer, until an average diameter of oily droplets below 0.4 µm is obtained.

The average diameter of the oily droplets is determined by the traditional granulometry measurement.

The optimal emulsifying concentration and the operating parameters of the homogenizers must be established by preliminary tests, in view of the diversity of the oily substances to be emulsified, the required concentrations and the equipment to be employed.

Only the combination of saponins+homogenization n°1+ homogenization n°2 allows to obtain a fluid and stable aqueous emulsion containing 40% of the oily phase, with less than 1% of vegetal emulsifier.

Thus, if another emulsifier is used, one of the 2 homogenization steps is lacking, or the indicated values are not complied with, the mentioned result cannot be obtained.

It is not at all obvious that the combination of these 3 elements ensures the achievement of the intended purpose. Then, neither was this developed before.

Below a description is given of some of the results observed with combinations differing from those in the invention, whereby the example mentioned in paragraph 4 is taken as a basis.
If a performing chemical emulsifier is used, for example on the basis of polyglyceric esters, it is not possible to use less than 3% of emulsifier, all other things remaining equal.
If one of the two homogenizations is not performed, or the indicated values for the emulsion droplets size are not taken into account, the 40% value of the oily phase with 1% of saponins cannot be achieved: a more or less significant part of the oily phase is readily visible at the surface of the emulsion, so that it becomes inappropriate for use.

Advantageously, at least one hydrophilic additive is added to the mix of hydrophilic components and at least one lipophilic additive is added to the mix of lipophilic components.

Additives are defined as supplementary substances such as preservatives, anti-oxidizers, sequestrants, etc., which ensure the preservation of the active substance.

Instead of additives, another preservation means can be used, such as a sterilization step of the whole of the homogenized emulsion.

The obtained emulsions are always milky.

In some applications, it is possible or recommended to use at least one natural or synthetic co-emulsifier in addition to the saponins.

It should finally be noted that the very fluid emulsions in the invention may serve as a basis for the production of gels or creams by the addition of a thickener(s) suitable for their application.

Manufacturing Example of an Emulsion According to the Invention Process

An aqueous emulsion of vegetal oil of 40% is made.

The emulsion components and their mass % are as follows.

Hydrophilic components—Demineralized water (continuous phase): 58.7%—Pure saponins (emulsifier): 0.8% Lipophilic components—Vegetal oils (dispersed phase): 40.0%—Microcare MTD 2 of Thor (preservative): 0.5% Total: 100.0%. The hydrophilic components and the lipophilic components are separately mixed in order to obtain homogeneous phases. The homogenization n°1 of the two phases is performed with a rotor stator type mixer of the Ultra-Turrax trademark, at 20.000 revolutions/minute. The homogenization n°2 of the preceding mix is performed with a high-pressure mixer of the APV trademark, in recycling mode, with a service pressure of 600 bar.

A fluid and stable milky emulsion is obtained.

The homogenization times must be experimentally established and depend on the nature of the vegetal oils and the characteristics of the homogenizers.

The values for the different mixes with the above-stated equipment are provided below for lots of 1 kg each.

Mixa: sunflower oil 50%+olive oil 50%

Mix b: sunflower oil 25%+Shea olein 35%+Argan oil 40%

Minimum homogenization times

|  | Homogenization no 1 | Homogenization no 2 |
|---|---|---|
| Mix a | 10 minutes | 16 minutes |
| Mix b | 10 minutes | 22 minutes |

The invention claimed is:

1. A manufacturing process for making a stable aqueous emulsion from an oily active substance for cosmetic, food or pharmaceutical use, said process comprising the steps:
   mixing hydrophilic components comprising water with a quantity of an emulsifier to form a first intermediate mixture;
   mixing lipophilic components comprising an oily active substance to form a second intermediate mixture;
   obtaining a first homogenization by combining the first intermediate mixture with the second intermediate mixture and using a rotatable mixer or an ultrasonic mixer and mixing the combined first intermediate mixture and second intermediate mixture until a combined mixture having a first state comprising oily droplets with an average diameter of below 6 μm is obtained; and
   obtaining a second homogenization by further mixing the combined mixture with a high pressure homogenizer until a second state comprising oily droplets having an average diameter of below 0.4 μm is obtained;
   wherein saponin is the sole emulsifier used in the manufacturing process and has a concentration of less than 1% by weight of the stable aqueous emulsion, and
   wherein the lipophilic components have a concentration of 40% or greater by weight of the stable aqueous emulsion.

2. The process according to claim 1, wherein the hydrophilic components comprise at least one hydrophilic additive and the lipophilic components comprise at least one lipophilic additive.

3. The process according to claim 1, wherein the combined mixture in the second state is sterilized.

4. The process according to claim 1, wherein the lipophilic components comprise sunflower oil and olive oil.

5. The process according to claim 1, wherein the lipophilic components comprise Shea olein oil.

6. The process according to claim 1, wherein the lipophilic components comprise Argan oil.

7. The process according to claim 1, wherein the saponin is a vegetal emulsifier.

8. The process according to claim 1, wherein the aqueous emulsion has a milky appearance.

9. A manufacturing process for making a stable aqueous emulsion from an oily active substance for cosmetic, food or pharmaceutical use, said process comprising the steps:
   mixing hydrophilic components comprising water with a quantity of an emulsifier to form a first intermediate mixture;
   mixing lipophilic components comprising an oily active substance to form a second intermediate mixture;
   obtaining a first homogenization by combining the first intermediate mixture with the second intermediate mixture and using a rotatable mixer or an ultrasonic mixer and mixing the combined first intermediate mixture and second intermediate mixture until a combined mixture having a first state comprising oily droplets with an average diameter of below 6 μm is obtained; and
   obtaining a second homogenization by further mixing the combined mixture with a high pressure homogenizer until a second state comprising oily droplets having an average diameter of below 0.4 μm is obtained;
   wherein saponin is the sole emulsifier used in the manufacturing process and has a concentration of less than 1% by weight of the stable aqueous emulsion, and
   wherein the lipophilic components have a concentration of 40% or greater by weight of the stable aqueous emulsion and sunflower oil.

10. A manufacturing process for making a stable aqueous emulsion from an oily active substance for cosmetic, food or pharmaceutical use, said process comprising the steps:
    mixing hydrophilic components comprising water with a quantity of an emulsifier to form a first intermediate mixture;
    mixing lipophilic components comprising an oily active substance to form a second intermediate mixture, said lipophilic components comprising sunflower oil with olive oil or Shea olein oil;
    obtaining a first homogenization by combining the first intermediate mixture with the second intermediate mixture and using a rotatable mixer or an ultrasonic mixer and mixing the combined first intermediate mixture and second intermediate mixture until a combined mixture having a first state comprising oily droplets with an average diameter of below 6 μm is obtained; and
    obtaining a second homogenization by further mixing the combined mixture with a high pressure homogenizer until a second state comprising oily droplets having an average diameter of below 0.4 μm is obtained;
    wherein saponin is the sole emulsifier used in the manufacturing process and has a concentration of less than 1% by weight of the stable aqueous emulsion, and
    wherein the lipophilic components have a concentration of 40% or greater by weight of the stable aqueous emulsion.

* * * * *

UNITED STATES PATENT AND TRADEMARK OFFICE
CERTIFICATE OF CORRECTION

Page 1 of 1

PATENT NO. : 11,000,046 B2
APPLICATION NO. : 14/653834
DATED : May 11, 2021
INVENTOR(S) : Epiphani It is certified that error appears in the above-identified patent and that said Letters Patent is hereby corrected as shown below:

On the Title Page

Item (73), Line 1, change "JEAN-CLAUDE" to -- JEAN-CLAUDE EPIPHANI --.

Signed and Sealed this
Sixteenth Day of November, 2021

Drew Hirshfeld
*Performing the Functions and Duties of the*
*Under Secretary of Commerce for Intellectual Property and*
*Director of the United States Patent and Trademark Office*